United States Patent [19]

Kim et al.

[11] Patent Number: 5,116,361
[45] Date of Patent: May 26, 1992

[54] SULFONATED POLYETHYLENEOXIDE-SUBSTITUTED POLYMERS WITH IMPROVED BLOOD COMPATIBILITY

[75] Inventors: Young-Ha Kim; Seo-Young Jeong; Kwang-Duk Ahn; Dong-Keun Han, all of Seoul, Rep. of Korea

[73] Assignee: Korea Institute of Science and Technology, Seoul, Rep. of Korea

[21] Appl. No.: 534,242

[22] Filed: Jun. 7, 1990

[30] Foreign Application Priority Data

Jun. 14, 1989 [KR] Rep. of Korea ............... 89-8518

[51] Int. Cl.$^5$ .............................. A61F 2/06
[52] U.S. Cl. .............................. 623/1; 623/11; 623/12; 623/66; 604/266; 523/105
[58] Field of Search .............. 623/1, 11, 12, 66; 604/266; 523/105; 427/2

[56] References Cited

U.S. PATENT DOCUMENTS

| | | | |
|---|---|---|---|
| 3,886,947 | 6/1975 | Sawyer | 623/66 |
| 4,743,258 | 5/1988 | Ikada et al. | 623/1 |
| 4,795,475 | 1/1989 | Walker | 427/2 |
| 4,882,148 | 11/1989 | Pinchuk | 604/266 |
| 4,965,112 | 10/1990 | Brinkman et al. | 427/2 |
| 5,017,664 | 5/1991 | Grasel et al. | 604/266 |

OTHER PUBLICATIONS

Y. Mori et al., TASAIO, 24, pp. 736-745 (1978), vol. XXIV.
Y. Mori, et al., Trans. ASAIO, 28, pp. 459-463 (1982), vol. XXVIII.
T. Okano et al., J. Biomed. Mater. Res., 15, pp. 393-402 (1981).
M. D. Lelah et al., J. Biomed. Mater. Res., 20, pp. 433-468 (1986).
P. N. Sawyer et al., Amer. J. Physiol., 175, 113-117 (1953).
F. J. Walker et al., Biochem. Biophys. Res. Commun., 83, pp. 1339-1346 (1987).
C. Fougnot et al., Ann. Biomed. Eng., 7, pp. 429-439 (1979).
M. D. Lelah et al., J. Colloid Interface Sci., 104, pp. 422-439 (1985).
J. M. Harris, J. Macromol. Sci., C(25) 3, pp. 325-373 (1985).
L. Smith et al., J. Appl. Polym. Sci., 26, pp. 1269-1276 (1982).
C. Nojiri et al., ASAIO J., 10, pp. 596-601 (1987).

Primary Examiner—Randall L. Green
Assistant Examiner—Paul Prebilic
Attorney, Agent, or Firm—Oblon, Spivak, McClelland, Maier & Neustadt

[57] ABSTRACT

Novel sulfonated polyethyleneoxide-substituted polymers having improved blood compatibility are provided. The polymers are produced by substituting a polymeric substrate having active sites of amide or acid amide group, such as polyurethane, polyamide and polyacrylamide, with sulfonated polyethyleneoxide PEO-SO$_3$H.

The polymers according to the present invention are valuable as construction materials of the artificial organs for the circulatory system in contact with blood, such as artificial hearts, artificial blood vessels, artificial kidneys, etc.

10 Claims, No Drawings

SULFONATED POLYETHYLENEOXIDE-SUBSTITUTED POLYMERS WITH IMPROVED BLOOD COMPATIBILITY

BACKGROUND OF THE INVENTION

1. Field of the Invention

The present invention relates to novel modified polymers having superior blood compatibility produced by substituting polymeric substrates having active sites of amide or acid amide groups, such as polyurethane, polyamide and polyacrylamide, with sulfonated polyethyleneoxide PEO—$SO_3H$, and a process for the preparation of the same modified polymers.

It has been found from the results of in vitro and ex vivo tests that the modified polymers of the invention show attributing to the synergistic effects of the exclusion of the proteins and platelets by the hydrophilic polyethyleneoxide polymers and the antithrombogenic action of the sulfonate anions when the modified polymers are in contact with blood.

The modified polymers according to the invention are useful especially as a variety of medical materials such as materials of the artificial organs for the circulatory system in contact with blood, e.g., artificial hearts, artificial blood vessels, artificial heart valves, artificial blood oxygenaters, artificial kidneys, etc. The modified polymers also are useful as construction and coating materials of the medical devices and instruments to be inserted into blood vessels such as vein catheters, intra-aortic balloon pumps, and artery catheters. When using the modified polymers of the inventions, the polymers can decrease significantly the thrombogenic action (thrombus) and, thus, prevent well undesirable side effects of the blood vessel occlusion.

The modified polymers of the invention can be prepared by introducing a PEO derivative having functional groups capable of reacting with the active sites of a polymeric into said polymeric substrate, and then reacting the substrate with a suitable sulfonic acid derivative, or by directly reacting the substrate with a PEO derivative having both functional groups capable of reacting with the active sites and a sulfonate group in a single pot step. Where the PEO derivative reacts with the above polymeric substrate, at the sites of the free monofunctional group introduced by the reaction of the substrate with diisocyanate or diacid chlorides, the reaction may proceed well under mild conditions.

Useful PEO derivatives may include PEO and its amines, p-toluenesulfonic ester, acid chlorides, isocyanates, epoxy, or halogen derivatives, etc. The sulfonate derivatives capable of reacting with PEO derivatives may include sulfites and their salts, bisulfites and their salts, aminoalkylsulfonic acid, hydroxyalkylsulfonic acid, and alkylsultone, etc. These sulfonate derivatives can be selected depending upon the nature of the functional groups of the PEO derivative introduced.

Medical materials require outstanding physical and mechanical characteristics, stability in vivo, sterilizability, and biocompatibility. Among these characteristics, biocompatibility is the most critical factor, supressing the rejection symptoms apt to naturally occur when the materials are brought into contact with human body tissues and/or blood.

When the blood vessel is destroyed or when blood is in contact with a foreign substance, the thrombus is generated due to the blood clotting.

Although the mechanism of the thrombus (blood clotting) has not yet been known in detail, it may be summarized as shown in the following diagram.

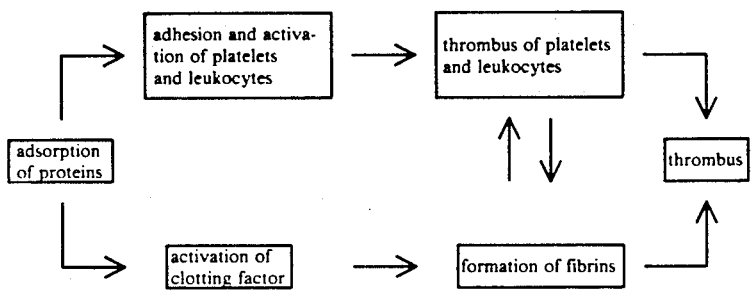

As shown in the above diagram, it is understood that the thrombus starts with the adsorption and activation of the blood proteins and platelets, followed by the activation of the coagulation factor. The thrombus ends in the formation of a network-structured fibrins in the presence of erythrocytes and leukocytes.

The thrombus may and can cause fatal problems like the blood vessel occlusion due to emboli when using certain materials as construction materials for internal circulatory system organs such as artificial hearts, artificial blood vessels, artificial kidneys and artificial blood oxygenaters, or other medical devices and/or instruments to be inserted into the blood vessels. Accordingly, the development of a material having superior blood compatibility or antithrombogenicity, capable of supressing the thrombus in contact with blood has hitherto been desired strongly.

2. Description of the Prior Art

In general, polymeric materials with blood compatibility which have hitherto been studied can be classified into two classes. One is the material supressing the adsorption and activation of the blood components, inter alia, proteins and platelets, as the material naturally having blood compatibility. Pseudointima-forming materials have also been studied, utilizing blood compatibility of a pseudointramembrane formed on the surface of the materials. The other is the material wherein physiologically active materials such as heparin, prostaglandin, and urokinase, which suppress thrombus are immobilized or slowly released onto the surface of the substrate to obtain desired blood compatibility.

Artificial blood vessels manufactured of polyester fabrics or expanded tetrofluoroethylene fluorocarbon polymer initially cause thrombus occurred on the surface thereof in contact with blood. The clotting layer resulted from the thrombus is the so-called pseudointima which has blood compatibility. These materials are hardly applied to the blood vessels in a small diameter or the blood vessels having a slow blood flow rate. Catheters using a physiologically active material such as heparin and development of the material were reported by Y. Mori et al., in *Trans. ASAIO*, 24: 736-745, (1978). However, there are found many limitations and inferiority in their effects due to the loss of physiologically active materials and the decrease of their activity.

Accordingly, a number of studies have been made to develop the materials having essentially superior blood compatibility.

Blood compatibility of a material is determined depending on the physiochemical structure of its surface, and significantly affected by its polarity, surface energy, surface electrical charge, hydrophilicity and hydrophobicity, the surface smoothness and porosity, and the like.

Surface free energy of a material is one of the important factors for determination of the blood compatibility. Hydrogels containing a lot of water are known as the materials having good blood compatibility since they exhibit a very low interfacial energy at the time of the interaction with blood. However, since those hydrogels have poor processing properties and mechanical strength, studies for the methods of grafting or coating on the substrate surface have been made.

Particularly, a number of studies have been made of PEO, a hydrophilic polymer. An antithromobogenic material was reported, which is prepared by grafting PEO on the surface of a polyvinyl chloride resin (Nagaoka et al., *Trans. ASAIO* 28: 459-463, (1982)). They emphasized in the report that the adhesion of the proteins and plaletets in the blood components could be suppressed by the excluded volume effect and the dynamic movement of hydrophilic PEO polymer chains grafted on its surface.

On the other hand, it has been reported that a polymer having a micro domain hydrophilic/hydrophobic structure can supress the activation of the proteins and platelets in the blood components and, thus, results in good antithrombogenic properties.

T. Okano et al. reported that a polystyrene-polyhydroxy ethylmethacrylate block copolymer has good antithrombogenic properties [T. Okano et al., *J. Biomed. Mater. Res.*,15: 393-402 (1981)].

In addition, polyurethane polymerized from a polyol/diisocyanate shows relatively antithrombogenic properties owing to its hydrophilic/hydrophobic structure [M. D. Lelah et al., *J. Biomed. Mater. Res.*,20: 433-468, (1986)]. Particularly, the polyurethane has outstanding mechanical characteristics. Therefore, it is now widely used as a material for constructing medical devices and instruments such as artificial hearts, intra-aortic balloon pumps, and blood vessel catheters to be in contact with blood.

On the other hand, it has been reported that blood components and blood vessel endothelial cells are negatively charged and, therefore, supression of the clotting in the blood vessels is owing to the electrical repulsion between the components and the cells [P. N. Sawyer et al., *Amer. J. Physiol.*,175:113, (1953)]. Accordingly, the polymer surface containing anions also exhibits good blood compatibility. For example, it has been reported, by F. J. Walker et al., in *Biochem. Biophys. Res. Commu.*,93:1339 (1987), that the unique suppression action of the thrombus by heparin, a linear anionic carbohydrate, is ascribed to the anions involved, such as sulfonate and aminosulfonate groups. This type of an anionic polymer includes sulfonated polystyrene [C. Fougnot et al. in *Ann Biomed. Eng.*,7: 429-439, (1979)]. According to another report, it is noted that the sulfonated polyurethane can improve considerably blood compatibility [S. L. Cooper et al., *J. Colloid Interface Sci.*,104: 422-439, (1985)].

SUMMARY OF THE INVENTION

The primary object of the invention is to provide a novel polymeric material having superior blood compatibility which eliminates the disadvantages encountered in the prior art techniques.

Another object of the invention is to provide a process for the preparation of a polymeric material having superior blood compatibility.

Still another object of the invention is to provide an extremely excellent material having an additional effect of native micro-domain hydrophilic/hydrophobic structure.

These and other objects of the invention can be achieved by the polymer modified according to the present invention, which can be prepared by reacting a polymeric substrate having amide or acid amide groups with diisocyanate or diacid chloride, and then reacting the substrate with a sulfonated polyethyleneoxide derivative at the sites of the resulting free functional groups. More alternatively, it is possible to obtain a high polymeric material having good blood compatibility, by binding aqueous sulfonated PEO directly to the above polymeric substrate. The material thus prepared possesses very superior blood compatibility owing to the synergistic effects resulted from the repulsion force of the negatively charged sulfonate anions, and from the suppression of the adsorption of the blood proteins and platelets by the PEO molecule. Particularly, use of polyurethane as the substrate can enhance blood compatibility due to the effect of an additional micro-domain hydrophilic/hydrophobic structure.

The modified polymers of the invention are entirely different from sulfonated polyurethane previously reported by S. L. Cooper, et al. in its structural features and design, because this deals with the effects of the anions formed by simply introducing a sulfonate group only.

The invention has however provided the synergistic effects of the hydrophilic PEO polymer as well as negatively charged sulfonate groups grafted on polyurethane.

The process according to the present invention proceed well in the mode of either a surface reaction or a solution reaction of a polymer molded in advance. The modified polymeric material prepared by a solution reaction according to the present invention may be used as molding and/or coating materials. These will be further described later.

Blood compatibility of the modified polymers of the invention was well evaluated by the in vitro and ex vivo tests. As a result, it was confirmed that the antithrombogenic properties of the modified polymers were increased in a great extent, and, therefore, this material could be used as the materials of artificial, circulatory, internal organs to be in contact with blood and the materials for use in molding and coating the medical devices and/or instruments to be inserted into the blood vessels.

DETAILED DESCRIPTION OF THE INVENTION

The present invention relates to a process for the preparation of polymers with highly improved blood compatibility, in which a polymeric substrate is modified by binding the sulfonate groups at the sites of a hydrophilic PEO polymer contained in the substrate. It has been found that the polymers thus modified show remarkably improved blood compatibility owing to the synergistic effects resulted from the antithrombogenic phenomena by the electrical repulsion of the sulfonate anions and by the suppression of the adsorption of plasma proteins and platelets due to the motion of soluble PEO polymer chains.

Hydrophilic polymer derivatives to be bound to the polymeric substrate may include synthetic polymers such as PEO, polyvinyl alcohol, polyhydroxyethylmethacrylate, poly (N-vinylpyrrolidone), and the like. Modified natural polymers, such as alkylcellulose, carboxyalkylcellulose, starch, agarose, and the like may also be used. Among them, however, PEO is most preferably used for the objects of the invention, because it has higher water-solubility and a better flexible chain structure. It can exhibit significant effects in suppressing the adsorption of the plasma proteins and platelets. The amounts and the molecular weight of the PEO polymer used are critical factors for blood compatibility. The most optimal blood compatibility is shown only when the polymer having a proper molecular weight is used, since the excluded volume effect and the movement of the chains become most optimal only under such condition. Generally, enhanced blood compatibility may be obtained when a PEO polymer having the molecular weight ranging from 100 to 20,000, preferably from 200 to 10,000.

As stated above, a sulfonated PEO polymer can be introduced into the polymeric substrate by simply reacting the substrate with a PEO polymer and subsequently with sulfonic acid. Alternatively, the sulfonated PEO polymer may be introduced to the polymeric substrate by reacting the substrate directly with a sulfonated PEO polymer in a single pot reaction. [The term "PEO polymer containing the sulfonate groups" used herein will often be referred to as the "sulfonated PEO" hereinafter.]

The polymeric substrate useful in the present invention may include polyurethane, polyamide or polyacrylamide having amide or acid amide groups containing a displaceable hydrogen atom. The hydrogen atom in an amide and acid amide group is considerably inactive but can be substituted depending on the reaction conditions applied. That is, the hydrogen atom can react directly with a strong nucleophilic compound, for example, an isocyanate or acid chloride compound. In addition, the hydrogen atom can be isolated by the action of a strong base, producing an amide or acid amide ion. These ions have chemically high activity; thus, they may be subject to displacement with halogens, epoxy, toluene sulfonic ester derivatives.

According to another aspect of the invention, it is more advantageous that after introducing a highly reactive functional group into a polymeric substrate, the substrate is reacted with a sulfonated PEO in a single pot reaction, or with a PEO polymer and then with sulfonic acid in a subsequential step of reaction. That is, the polymeric substrate may be reacted with a diisocyanate or diacid chloride compound to introduce a monoisocyanate group or monoacid chloride group into the substrate. These groups can be bound to a PEO polymer under mild conditions which can avoid of the damages to the resultant material and the PEO polymer thus obtained is preferably used for the purposes of the invention.

The sulfonated PEO having the functional groups capable of directly binding with the polymeric substrate employed and its derivatives can be prepared by various different methods. The commercially available PEOs have hydroxy groups at both ends of its chain. The hydroxy groups may be converted to a variety of functional groups by conventional methods [J. M. Harris, *J. Macromol. Sci.*, C(25)3: 325 (1985)]. The hydroxy groups can be substituted substantially with all possible functional groups. For example, the hydroxy groups may be converted to bromide groups by the reaction of them with thionyl bromide, to carboxyl groups by the oxidation of them with $KMnO_4$, to epoxy groups by the reaction of them with epichlorohydrin, or to isocyanate groups by the reaction of them with diisocyanate. The bromine atoms thus displaced can, in turn, be converted to amino groups by the reaction with ammonia. The carboxyl groups may be converted to acid chloride ones.

Likewise, it is possible to select a proper method for introducing a sulfonate group to a PEO derivative, depending on the types of the functional groups bound to PEO. Useful methods may include, for example, methods of reacting alkylsultone or sodium bisulfite with the hydroxy groups of PEO, of reacting the bromine atom of PEO with sodium sulfite, of reacting the isocyanate group with an aminoalkyl sulfonic acid or a hydroxyalkylsulfonic acid, or of bonding an expoxy group of PEO with sodium bisulfite or a hydroxy alkylsulfonic acid.

The following three methods for introducing a sulfonated PEO into a polymeric substrate may be available.

The first is featured by binding PEO with a free monofunctional group introduced by the reaction of a difunctional compound with a polymeric substrate. The difunctional compound may be the diisocyanates and diacid chlorides.

Reaction 1: Polyurethane/polyamide/polyacrylamide

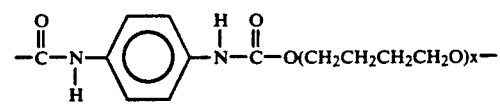

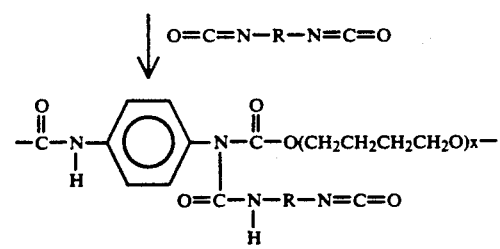

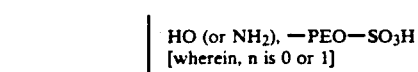

-continued

Reaction 1: Polyurethane/polyamide/polyacrylamide

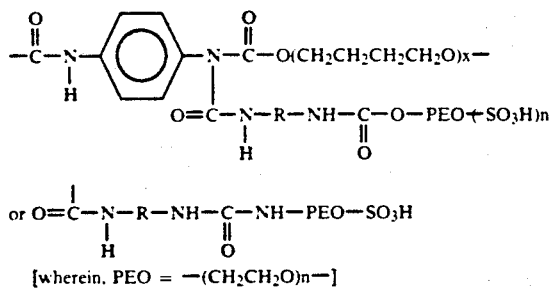

[wherein, PEO = $-(CH_2CH_2O)_n-$]

Useful diisocyanates may include hexamethylene diisocyanate (HMDI), toluene diisocyanate (TDI), diphenylmethane diisocyanate (MDI). Organic stannous derivatives or amines may preferably used as the catalysts for the polyurethane modification. The above reaction may proceed under mild conditions without the damages to the material used.

Reaction 2: Polyacrylamide/polyamide/polyurethane

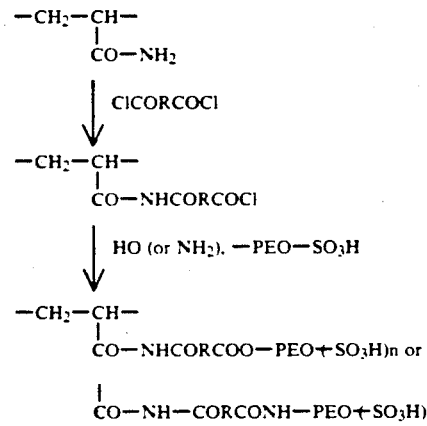

Useful diacid chlorides may include diacid chlorides of a fatty acid, wherein R represents 2-30 carbon atoms.

The second is featured by reacting a polymeric substrate with a PEO polymer having an isocyanate or acid chloride group which can be reacted directly with the substrate.

Reaction 3: polyurethane/polyamide/polyacrylamide

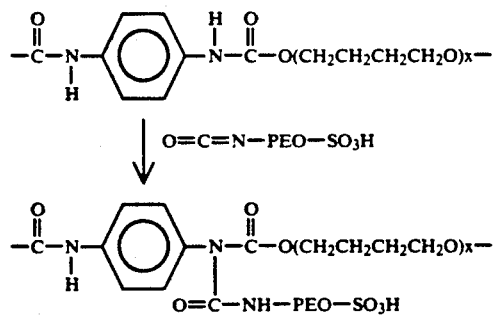

Polyurethane, polyamide, or polyacrylamide react with the isocyanate group to be converted to a urea derivative.

Reaction 4: Polyacrylamide/polyamide/polyurethane

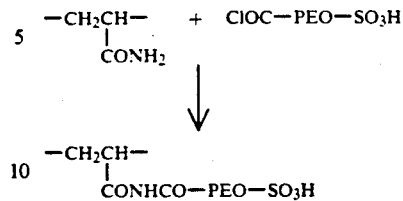

The third is featured by treating a polymeric substrate with a strong base to introduce amide anions and then reacting the amide anions with a PEO derivative containing halogen, or an epoxy or toluenesulfonate group. Useful strong bases may include sodium and potassium hydride, sodium and potassium ethoxide, sodium and potassium butylate, methylmagnesium bromide, and the like.

Reaction 5: Polyamide/polyurethane/polyacrylamide

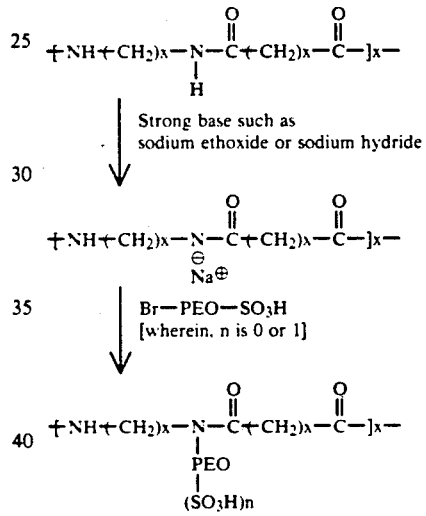

Reaction 6: Polyurethane/polyamide/polyacrylamide

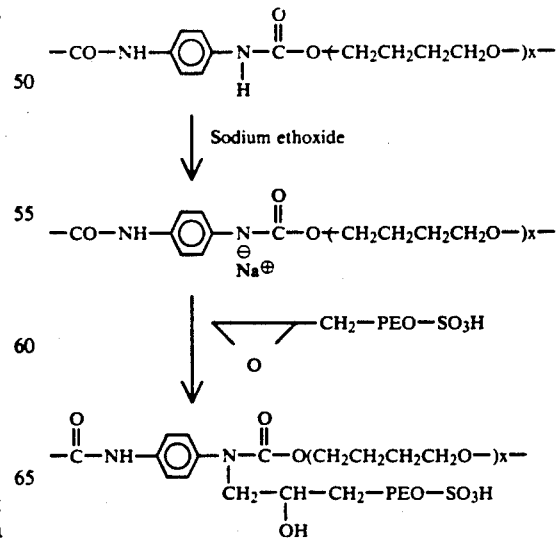

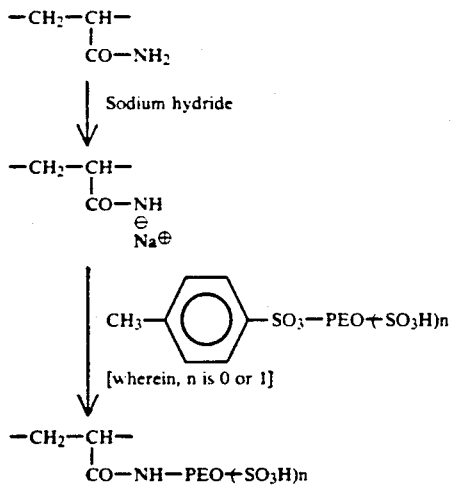

Reaction 7: Polyacrylamide/polyamide/polyurethane

[wherein, n is 0 or 1]

The modified polymer according to the invention can be prepared through a surface reaction on the polymeric substrate once molded. The polymers can be modified in solution in a proper solvent. The polymers thus modified are useful as the materials for use in molding and coating the polymeric substrate. Accordingly, in case of a surface reaction it should be careful so as to carry out the reaction in a medium in which the polymeric substrate is insoluble and it is preferred to select a medium having a lower swelling ability. Tetrahydrofuran, dimethylacetamide, or dimethylformamide is preferably used as a solvent of polyurethane. Formic acid is used as a solvent of polyamide. Water or alcohol is preferably used as a solvent of polyacrylamide. Therefore, the reaction medium may be selected depending on the type of the intended reaction, i.e., the surface or the solution reaction.

As previously described, the antithrombogenic property is developed by suppression of the adsorption of plasma proteins and platelets due to the electrical repulsion between anions such as sulfonate groups and the blood components. It is known that the sulfonate group is more effective than carboxyl group in terms of antithrombogenicity. Thus, the electrical density of the surface of a polymer, into which an anion or anions are introduced, also is an important factor in determining the antithrombogenic properties.

Accordingly, blood compatibility depends significantly upon the substitution degree of the sulfonated polyethyleneoxide with respect to the amide or acid amide groups in the polymeric substrate of the invention. In principle, blood compatibility increases with the increase of the degree of the substitution. On the other hand, water solubility and flexibility of the substrate also increase as the degree of the substitution increases. There are no particular changes in water solubility and mechanical characteristics of the substrate in the case of a surface reaction. Therefore, methods for controlling the degree of the substitution should be selected depending on the final usage of the product of the invention and the type of the product. In the case of a surface reaction, the degree of the substitution capable of resulting in superior blood compatibility is 60-95% with respect to the functional groups on the surface. For a bulk reaction in solution, it is possible to obtain molding materials having superior blood compatibility, which have been modified in 5-25% of the degree of the substitution and molding or coating materials which have been modified in 30-90% of the degree of substitution.

Such modified polymers may be used as the medical construction and coating materials, such as films, sheets, tubes, fibers, fibers, and hollow fibers. Therefore, those polymers can be utilized as various materials for the artificial, circulatory, internal organ systems to be in contact with blood, such as artificial hearts, artificial blood vessels, artificial heart valves, artificial blood oxygenaters, and artificial kidneys. The polymers may also be used for construction and coating materials of medical devices/instruments to be inserted into the blood vessels (e.g., vein catheters), intra-aortic balloon pumps, and artery catheters. The modified polymers of the invention do not produce any side effects due to significantly decreased thrombus.

Analysis for the Contact Angle of Material (Hydrophilicity and Hydrophobicity)

As previously discussed, biocompatibility, particularly, blood compatibility of a material is determined by physicochemical structures of the surface of the material. Hydrophilicity and hydrophobicity of the material are the most important factors. The hydrophilicity and hydrophobicity are analyzed by the contact angles defined at the time of the contact with liquid. Hydrophilicity and hydrophobicity of the modified polymers of the present invention are determined by the dynamic contact angles following the Wilhelmy Plate method [L. Smith et al., J. Appl. Polym. Sci., 26:1269, (1982)]. This method teaches how to determine the advancing and the receding contact angles by precisely detecting changes of the weight when the material is soaked into and taken out of water.

The higher the advancing contact angle is, the greater hydrophobicity of the material is, whereas the lower the receding contact angle is, the higher hydrophilicity of the material is. Hydrophilicity of the modified polymers according the present invention significantly increases by binding them with PEO derivative and, particularly, a complete "wetting" phenomena is exhibited by introducing a sulfonate groups into the polymers. Thus, it si suspected that the interaction between a modified polymer and blood is more decreased. The contact angles will be discussed in the working examples hereinafter.

Analysis for the Antithrombogenic Properties of Materials (Blood Compatability)

A number of in vitro and ex vivo analytical methods for the antithrombogenic properties of many materials have been reported in literature [Guidelines for Blood-Material Interactions, National Institutes of Health, Edition No. 85-2185, (1985)]. Evaluation of the antithrombogenicity in accordance with the present invention is performed by the in vitro activated partial thromboplastin time (APTT), prothrombin time (PT), platelet adhesion, and ex vivo arterio-arterial shunt tests.

The APTT determination was carried out by using the Fibrometer Method as follows [R. G. Mason et al., Amer. J. Path., 69:271 (1972)]. A sample material was contacted with standard plasma (300 ul) for an hour to give a plasma sample (0.1 ml, 37° C.). This plasma sample was then added to preheated partial thromboplastin (0.1 ml) for 2 min. After 30 sec in exact, an aqueous 0.025M calcium chloride solution (0.1 ml) was added to the mixture, and the coagulation time was determined by using a fibrintimer. The longer APTT exhibited an higher antithrombosis activity.

The PT was evaluated by monitoring the one-stage prothrombin time [J. B. Miale, Lab. Med. Hematology, 1267, (1982)]. Thromboplastin (0.1 ml) was mixed with an aqueous 0.025M calcium chloride solution (0.1 ml) and then preheated at 37° C. A plasma sample (0.1 ml) which has been obtained by using the same method as that in the APTT evaluation is added to the mixture. The coagulation time is determined with a fibrintimer. The longer PT also exhibited better blood compatibility.

The adhesion test of platelets was performed by detecting the amount of platelets adhered to each material. A sample polymer material was soaked at 37° C. for 3 hours into plateletrich plasma (PRP) obtained through centrifugation of whole human blood, then transferred into phosphate buffered saline (PBS), and washed at 37° C. for 1 minute with shaking. The sample thus treated was soaked into an aqueous 2% glutaldehyde solution in PBS buffer for 2 hours to immobilize adhered platelets onto the surface of the polymer material, then dehydrated with an ethanolic, aqueous solution, freeze-dried, and then observed through a scanning electron microscopy.

The ex vivo arterio-arterial shunt method is to simply and rapidly evaluate blood compatibility of a material under animal experimental conditions using rabbits [C. Nojiri et al, *ASAIO J.* 10:596, (1987)].

Both ends of a sample tube (inner diameter: 1.5 mm, outer diameter: 2.0 mm, length: 30 cm) are inserted into the exposed carotid artery of a rabbit to circulate blood in the form of a shunt. The occlusion time of the blood vessel is defined as the time the blood flow decreases to zero after circulating the blood controlled at a rate of 2.5 ml/min. The longer occlusion time exhibited better blood compatibility.

The present invention will be described and illustrated in greater detail by means of the following non-limiting working examples.

EXAMPLE 1

A polyurethane sheet of 2 cm$^2$ in area and 1 mm in thickness (Pellethane 2363-80A available from The Upjohn Company, Kalamazoo, Mich.) was refluxed in boiling methanol for 18 hours to remove surface impurities and then added to toluene (120 ml). After adding hexamethylenediisocyanate (HMDI) (2 ml) and stannous octoate (1 ml) to the solution, the resultant mixture was reacted at 20°-40° C. for 1-2 hours, and then sufficiently washed with toluene. The surface was observed through attenuated total reflection-Fourier transform infrared spectroscopy (ATR-FTIR). As a result, free functional groups of the introduced monoisocyanates could be detected.

The resultant sheet was reacted with a mixture of HO—PEO200—SO$_3$H (3 ml) and triethylamine (1 ml) in toluene (120 ml) at 20°-40° C. for 2 hours. Polyethyleneoxide (M.W. 200, available from Aldrich Chemical Company, Inc., U.S.A.) (4 g) was dissolved in dimethylsulfoxide (12.5 ml) at 85° C. with stirring, and then reacted with a mixture of 1,3-propanesultone (2.5 g) and sodium carbonate (1 g) at 85° C. for 16 hours. The reaction mixture was extracted with methanol to give HO—PEO200—SO$_3$H.

The advancing and the receding contact angles of the polyurethane sheet thus modified were 29.2° and "wetting", respectively. These angles were found to have significantly been decreased as compared with the advancing contact angle (86.3°) and the receding contact angle (40.6°) of the non-modified, original polyurethane sheet, resulting in typical hydrophilicity. In addition, APTT and PT of the untreated sheet were 35.8 sec and 13.2 sec, respectively (APTT and PT of the standard plasma were 36.0 sec and 13.0 sec, respectively), whereas APTT and PT of the modified sheet increased to 48.6 sec. and 15.0 sec., respectively. Adhesion of the platelets was significantly lowered. Likewise, the occlusion time of a rabbit arterioarterial shunt of the polyurethane tube of which inner surface has been treated (Royalthene R380 PNAT, available from Uniroyal, Inc., inner diameter: 1.5 mm, outer diameter: 2.0 mm, length: 30 cm) was 360 minutes; this indicates a significant increase as compared with that of 50 minutes for the untreated tube.

Thus, from the above APTT, PT, platelet adhesion, and rabbit arterio-arterial shunt tests for both polyurethane sheets and tubes before and after the reaction, it could be found that blood compatibility of the polyurethane materials has significantly improved through the modification according to the present invention.

EXAMPLE 2

The same procedures as described in Example 1 was carried out, except that NH$_2$—PEO 3500—SO$_3$H was used in place of HO—PEO 200—SO$_3$H. The contact angle was as low as that shown in Example 1, and the APTT and PT equal to those in Example 1 exhibited. Therefore, blood compatibility was also excellent.

NH$_2$—PEO 3500—SO$_3$H was prepared by reacting NH$_2$—PEO—NH$_2$ (M.W. 3500, available from The Sigma Fine Chemicals, USA) with an equivalent amount of 1,3-propanesultone in the presence of a base catalyst.

EXAMPLE 3

In a manner similar to that described in Example 1, a polyurethane sheet reacted with HMDI was reacted with a mixture of PEO 200 (2 g) and stannous octoate (1 ml) in benzene (120 ml) at 20°-40° C. for 4 hours. The sheet was taken out of the reaction mixture, washed sufficiently with benzene, ethanol and water in order, and reacted with a reaction system containing isopropyl alcohol (50 ml), dimethylsulfoxide (2 ml), sodium carbonate (2 g), and 1,3-propanesultone (2 g) at 60°-80° C. for 4 hours. The surface contact angles and blood compatibility of the modified sheet were excellent to the extent of those obtained in Example 1.

EXAMPLE 4

A solution of polyurethane (5 g) dissolved in dimethylacetamide (100 ml) was subjected to bulk reaction after adding hexamethylenediisocyanate (6.3 ml) at 20°-50° C. for 1 week and then precipitated with anhydrous ether. The product (5 g) was dissolved in dimethylacetamide (100 ml) and then reacted in the same manner as described in Example 1. Also, it was reacted in turn with PEO and 1,3-propanesultone instead of HO—PEO 200—SO$_3$H. That is, PEO (5 g) was added to HMDI-reacted polyurethane (5 g) dissolved in dimethylacetamide (100 ml) and reacted at room temperature for 3 days. The reaction solution was precipitated with distilled water and dried. Subsequently, it was followed by reaction in mixture of dimethylsulfoxide (100 ml), 1,3-propanesultone (0.25 g), and sodium carbonate (0.1 g) at 40°-85° C. for 15-24 hours. The degree of substitution of the introduced sulfonate groups was about 25%.

The surface properties and blood compatibility of the polyurethane sheet coated with a 2% tetrahydrofuran solution of the polyurethane thus modified were equivalent to those obtained in Example 1.

COMPARATIVE EXAMPLE 1

Polyurethane was treated in the same manner as that described in Example 1, except for using HO—PEO 200—OH instead of HO—PEO 200—SO$_3$H. The advancing and the receding contact angles obtained from the reaction with PEO which has not been reacted with sulfonic acid were 29.9° and 19.9°, respectively, exhibiting an significant enhancement of hydrophilicity. However, these values were lowered as compared with the sulfonate group-containing polyurethane. Adhesion degree of the platelets was almost low as that of the polymer modified by the method of Example 1, and APTT and PT were 37.4 sec and 13.6 sec, respectively. These were similar to those of untreated polyurethane. The occlusion time of a rabbit arterio-arterial shunt of the modified polyurethane tube was extended to 120 min, but it was found to be shorter than the value obtained in Example 1.

From the foregoing results, polyurethane, which was initially reacted with only PEO exhibited a somewhat enhancement of blood compatibility owing to the decrease of the adhesion of platelets. However, it could be confirmed that blood compatibility of the polyurethane treated in this example was detracted due to lack of the anionic effect of sulfonate group, as compared with Example 1.

COMPARATIVE EXAMPLE 2

Polyurethane was treated in the same manner as Example 3, except for using dodecanediol instead of PEO200 and dibutyl tin dilaurate instead of stannous octoate as a catalyst. The advancing and the receding contact angles of polyurethane combined with highly hydrophobic dodecylalkyl chains and sulfonate ions, in place of PEO, were 68.0° and "wetting", respectively. This indicates that hydrophilicity of the polyurethane was highly enhanced owing to the sulfonate ions. APTT and PT of this polyurethane were 40.5 sec and 14.2 sec, respectively. These values were found to be increased as compared with those of the untreated polyurethane, but exhibited a decrease as compared with that of the modified polyurethane in Example 1. The occlusion time of a rabbit arterio-arterial shunt was 200 minutes, which showed a value between 50 minutes for the untreated polyurethane and 360 minutes for the modified polyurethane in Example 1. In other words, blood compatibility of the modified polyurethane substituted with hydrophobic dodecylalkyl and sulfonate groups was significantly improved as compared with that of untreated polyurethane owing to the introduction of the sulfonate groups. Improvements in the effects thereof was inferior to those of the modified polyurethane to which the hydrophilic PEO and the sulfonate groups bound. It was found that the reason was due to lack of the adhesion effect of the platelets owing to PEO.

EXAMPLE 5

A polyacrylamide beads of 50-100 mesh in size (1 g) were reacted with adipoyl chloride (2 g) in benzene (120 ml) at room temperature and then with HO—PEO200—SO$_3$H (2 g) at 40° C. Blood compatibility was confirmed to have been greatly improved from the extension of the APTT and PT.

EXAMPLE 6

The same polyurethane sheet as used in Example 1 was reacted with a mixed solution of HSO$_3$—PEO—CONH—(CH$_2$)$_6$—N=C=O (3 g) in chloroform and stannous octoate (1 ml) in benzene (120 ml) at 20°-40° C. for 2-6 hours. HSO$_3$—PEO—O—CONH—(—CH$_2$—)$_6$—N=C=O was obtained by reacting HSO$_3$—PEO—OH prepared in Example 1 with an equivalent amount of HMDI in dioxane.

The advancing and receding contact angles of the treated sheet were 40.5° and "wetting", respectively. In addition, APTT and PT were 48.6 sec and 15.4 sec, respectively. Adhesion of platelets was low. Blood compatibility was found to be excellent based on a rabbit arterio-arterial shunt experimental test conducted by using the same polyurethane tube as in Example 1. The test exhibited the occlusion time of 340 minutes.

EXAMPLE 7

A solution of polyurethane (5 g) in dimethylacetamide (200 ml) was subjected to bulk reaction using the same chemical and reagents as used in Example 6 under the same conditions. The degree of the substitution of the introduced sulfonate groups was 45%.

A solution of the modified polyurethane which was purified according to the same method as in Example 4 was applied on the sheet and tube to be tested. Blood compatibility was found equivalent to that in Example 6.

EXAMPLE 8

The same polyurethane sheet as used in Example 1 was reacted with sodium hydride (1 g) in toluene (120 ml) at 0°-5° C. for 20 minutes under nitrogen atmosphere. A solution of Br—PEO1000—SO$_3$H (3 g) in chloroform was added slowly to the above reaction mixture to effect a reaction between them. The reaction mixture was washed with toluene, alcohol and water in order, and then dried.

Br—PEO1000—SO$_3$H was prepared in the following manner. Both hydroxy ends of the PEO chain having a molecular weight of 1000 (Aldrich Chemical Company, Inc., USA) were contacted with excess amounts of theronyl bromide in toluene in the presence of triethylamine to give Br—PEO1000—Br. Two equivalent amounts of Br—PEO 1000—Br were reacted with an equivalent amount of sodium sulfite in an aqueous solution of ethanol to give Br—PEO1000—SO$_3$H.

The advancing and receding contact angles of the surface-modified polyurethane thus obtained were 28.7° and "wetting", respectively, which exhibit perfect hydrophilicity. APTT and PT of the polyurethane thus treated were 49.7 sec and 15.2 sec, respectively. APTT and PT of the original polyurethane before treatment was 35.8 sec and 13.2 sec respectively. Accordingly, the increased antithrombogenic property could be confirmed based on the extended APTT and PT values. It was observed by a scanning electron microscopy that the adhesion of the modified polyurethane to platelets was significantly lowered as compared with that of the original polyurethane sheet prior to treatment based on an adhesion testing using PRP.

In addition, the inner wall of the same polyurethane tube as used in Example 1 was reacted with the same reagents and manner as used in the example by circulating the reagents into the tube. Circulation of blood through the treated tube by a rabbit arterio-arterial shunt showed the occlusion time of 360 minutes which was found to be significantly extended as compared with the occlusion time of 50 minutes for the untreated tube. From the above results, a material having superior blood compatibility can be obtained according to the present invention.

EXAMPLE 9

A solution of polyurethane (5 g) in dimethylformamide (200 ml) was reacted with sodium hydride (1 g) and Br—PEO1000—SO$_3$H 3 g) in order according to Example 8. The reaction mixture was subject to precipitation in excess of methanol. The separated precipitates were washed with water and then dried. Analysis for elements showed that the substitution degree of the sulfonate groups was 50%. The polymer thus modified was prepared in the form of 2% solution in dimethylformamide, and coated onto a polyurethane sheet and tube. The contact angles, APTT, PT, platelet adhesion, and the occlusion time of a rabbit arterio-arterial shunt were each determined. Blood compatibility was found to be equivalent to that in Example 8.

EXAMPLE 10

A Nylon 66 sheet of the same size as that of the polyurethane sheet used in Example 8 (E.I. du Pont de Nemour and Company, Inc., U.S.A.) was treated according to the method of Example 8. Hydrophilicity of the sheet increased owing to the decrease of the contact angles. Blood compatibility of the sheet was found equal to that obtained in Example 8 based on the platelet adhesion test.

EXAMPLE 11

The same reaction as in Example 8 was carried out, except that sodium ethoxide and

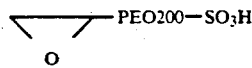

instead of sodium hydride and Br—PEO1000—SO$_3$H, respectively. The advancing and receding contact angles were 39.2 and "wetting", respectively. These values were indicative of the fact that hydrophilicity had been decreased due to the reduction of the molecular weight of the hydrophilic PEO to 200. APTT, PT and the platelet adhesion tests showed that blood compatibility was significantly improved to the extent comparable to that exhibited in Example 8. The occlusion time of rabbit arterio-arterial shunt was 350 minutes; this was suggestive of the fact that the material had excellent antithrombogenic properties.

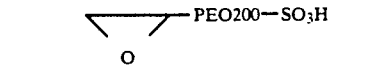

was prepared by reacting an equivalent amount of

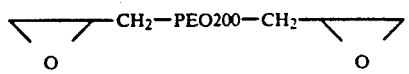

(product available from Polyscience Company, U.S.A.), with an equivalent amount of NH$_2$(CH$_2$)$_3$SO$_3$H in an aqueous basic catalyst solution.

As can be seen from the foregoing examples, the polymers, of the invention, combined with hydrophilic sulfonated PEO can exhibit superior blood compatibility owing to the synergistic effect resulted from their antithrombogenic action by sulfonate anions and from their supression action of the adhesion of proteins and platelets by the hydrophilic PEO. In contrast, from the polymers combined with only PEO, such effects could not be expected.

What is claimed is:

1. A modified polymeric material having improved blood compatibility, comprising a polymeric substrate having sulfonated polyethylene oxide groups substituted for amide or acid amide groups of said substrate.

2. The modified polymeric material of claim 1, wherein said polymeric substrate is selected from the group consisting of polyurethane, polyamide, polyacrylamide, and copolymers thereof.

3. The modified polymeric material of claim 1, wherein the substitution degree of the sulfonated polyethyleneoxide is 5–50% in the case of a bulk reaction and 50–95% in the case of a surface reaction, respectively.

4. A construction material of medical devices or instruments for use in contact with blood, comprising the modified polymeric material of any of claims 1 to 3.

5. An artificial heart comprising the modified polymeric material of any of claims 1 to 3.

6. An artificial blood vessel comprising the modified polymeric material of any of claims 1 to 3.

7. An artificial heart valve comprising the modified polymeric material of any of claims 1 to 3.

8. An artificial blood oxygenater comprising the modified polymeric material of any of claims 1 to 3.

9. An artificial kidney comprising the modified polymeric material of any of claims 1 to 3.

10. A blood vessel catheter comprising the modified polymeric material of any of claims 1 to 3.

* * * * *

UNITED STATES PATENT AND TRADEMARK OFFICE
CERTIFICATE OF CORRECTION

PATENT NO. : 5,116,361
DATED : May 26, 1992
INVENTOR(S) : Kim et al

It is certified that error appears in the above-identified patent and that said Letters Patent is hereby corrected as shown below:

Column 6, Reaction Scheme 1, delete "HO (or NH$_2$),-PEO-SO$_3$H", and insert --HO (or NH$_2$)-PEO-SO$_3$H--.

Column 6, Reaction Scheme 1, delete "[wherein, n is 0 or 1].

Column 7, Reaction Scheme 1, replace the formula

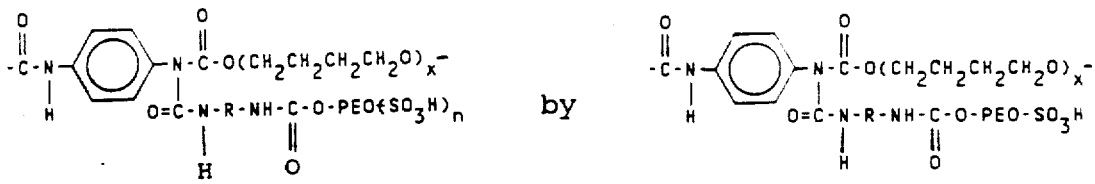

UNITED STATES PATENT AND TRADEMARK OFFICE
CERTIFICATE OF CORRECTION

PATENT NO. : 5,116,361
DATED : May 26, 1992
INVENTOR(S) : Kim et al

It is certified that error appears in the above-identified patent and that said Letters Patent is hereby corrected as shown below:

Column 7, Reaction Scheme 2, replace the formula

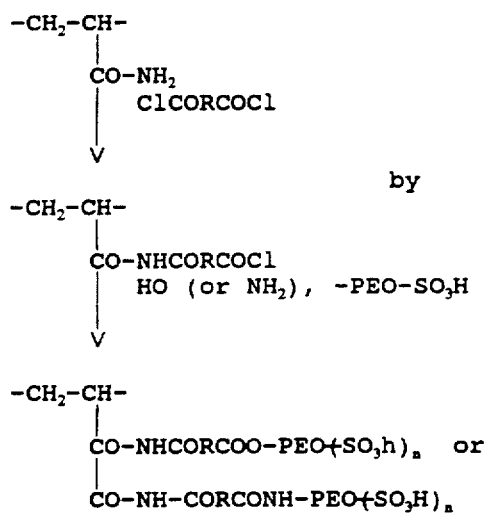 by 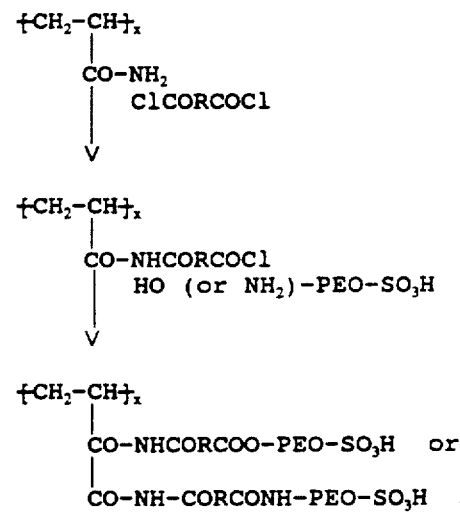

UNITED STATES PATENT AND TRADEMARK OFFICE
CERTIFICATE OF CORRECTION

PATENT NO. : 5,116,361

DATED : May 26, 1992

INVENTOR(S) : Kim et al

It is certified that error appears in the above-identified patent and that said Letters Patent is hereby corrected as shown below:

Column 8, Reaction Scheme 4, replace the formula

Column 8, Reaction Scheme 5, replace the formula

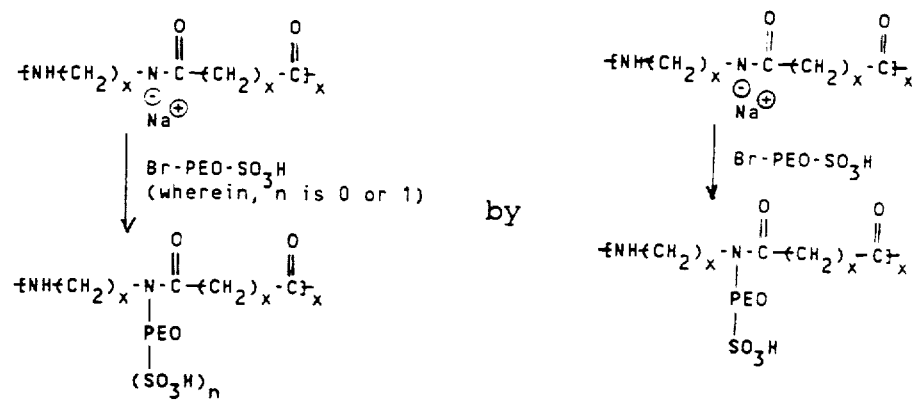

UNITED STATES PATENT AND TRADEMARK OFFICE
CERTIFICATE OF CORRECTION

PATENT NO. : 5,116,361

DATED : May 26, 1992

INVENTOR(S) : Kim et al

It is certified that error appears in the above-identified patent and that said Letters Patent is hereby corrected as shown below:

Column 9, Reaction Scheme 7, replace the formula

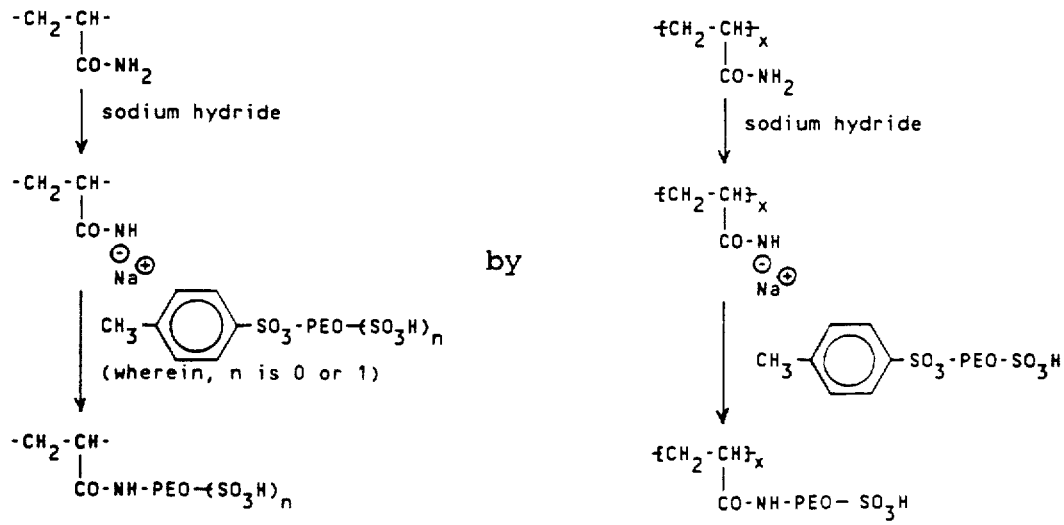

UNITED STATES PATENT AND TRADEMARK OFFICE
CERTIFICATE OF CORRECTION

PATENT NO. : 5,116,361

DATED : May 26, 1992

INVENTOR(S) : Kim et al

It is certified that error appears in the above-identified patent and that said Letters Patent is hereby corrected as shown below:

```
Column 10, line 45, delete "Thus, it si..." and, insert
          --Thus, it is...--.

Column 11, line 3, delete "antithrombosis", and insert
          --antithrombogenic--;
          line 17, delete "plateletrich", and insert
          --platelet-rich--;
          line 21, delete "glutaldehyde", and insert
          --glutaraldehyde--.

Column 12, line 12, delete "arterioarterial", and insert
          --arterio-arterial--.

Column 14, line 50, delete "theronyl", and insert
          --thionyl--.

Column 15, line 16, insert --(-- before "3 g)".
```

Signed and Sealed this

Sixteenth Day of November, 1993

Attest:

BRUCE LEHMAN

*Attesting Officer*    *Commissioner of Patents and Trademarks*